United States Patent [19]

Nelson et al.

[11] 4,011,243
[45] Mar. 8, 1977

[54] INTERMEDIATE IN THE OXIDATIVE PROCESS FOR THE PREPARATION OF 2-(5H-DIBENZO[a,d]CYCLOHEPTEN-5-ON-2-YL)ACETIC, PROPIONIC AND BUTYRIC ACIDS

[75] Inventors: Peter H. Nelson; Karl G. Untch, both of Los Altos, Calif.

[73] Assignee: Syntex (U.S.A.) Inc., Palo Alto, Calif.

[22] Filed: Sept. 8, 1975

[21] Appl. No.: 611,054

[52] U.S. Cl. .................. 260/340.9; 260/340.7; 260/469; 260/515 R; 260/590 FB; 260/599
[51] Int. Cl.² ...................................... C07D 317/72
[58] Field of Search ................. 260/340.9 R, 340.7

[56] References Cited

UNITED STATES PATENTS

| | | | |
|---|---|---|---|
| 3,833,655 | 9/1974 | Edenhofer | 260/340.9 X |
| 3,933,905 | 1/1976 | Brunet et al. | 260/340.9 X |

*Primary Examiner*—Ethel G. Love
*Attorney, Agent, or Firm*—Alan M. Krubiner; William B. Walker

[57] ABSTRACT

2-(5H-Dibenzo[a,d]cyclohepten-5-on-2-yl)acetic, propionic and butyric acids are prepared by oxidation of the corresponding 5-oxo- or ketal-protected oxoalcohols and aldehydes. The acid products exhibit anti-inflammatory, analgesic and anti-pyretic activity.

4 Claims, No Drawings

INTERMEDIATE IN THE OXIDATIVE PROCESS FOR THE PREPARATION OF 2-(5H-DIBENZO[a,d]CYCLOHEPTEN-5-ON-2-yl)ACETIC, PROPIONIC AND BUTYRIC ACIDS

DETAILED DESCRIPTION OF THE INVENTION

The present invention is concerned with a process for the preparation of 2-(5H-dibenzo[a,d]cyclohepten-5-on-2-yl) acetic, propionic and butyric acids. More specifically, the present invention concerns processes for the preparation of the compounds of the formula

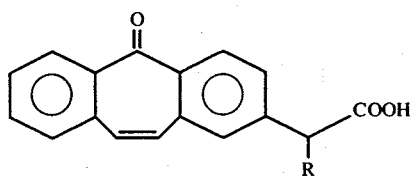

and salts thereof, wherein R is hydrogen, methyl or ethyl, from the corresponding 5-oxo- or ketal-protected oxoalcohols and aldehydes.

The compounds of Formula I exhibit anti-inflammatory, analgesic and anti-pyretic activity. Accordingly, compounds of formula I and compositions containing same are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, posttraumatic conditions, and gout. In those cases in which the above conditions include pain and pyrexia coupled in inflammation, the compounds of formula I are useful for the relief of these conditions as well as the inflammation.

The compounds of formula I are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus.

"Salts" of the carboxylic acids of Formula I refer to those salts prepared from inorganic and organic bases. Salts derived from inorganic bases include the alkali metal salts such as sodium, potassium and lithium; the alkaline earth salts such as calcium and magnesium; as well as the ammonium and copper salts. Those salts derived from organic bases include the ethanolamine, diethylamine, tris(hydroxymethyl) aminomethane, choline, caffeine, and lysine salts. A preferred subclass of salts of Formula I are those formed from pharmaceutically acceptable non-toxic bases.

The term "conventional ketal protecting group" refers to those ketal groups conventionally used in the art to protect a reactive ketone function, which groups are readily removable by acid hydrolysis. Classes of conventional ketal protecting groups contemplated by the above are dialkyl ketals (alkyl groups of from 1 to 6 carbon atoms) such as for example, dimethyl or diethyl ketals; alkylene ketals (alkylene of 2 to 4 carbon atoms optionally substituted with lower alkyl groups of 1–4 carbon atoms) such as for example, the ethylene, 1,3-propylene, 2,2-dimethyl-1,3-propylene, 1,4-butylene and 2,3-butylene ketals; and dibenzyl ketals.

The process of the present invention may be summarized in the reaction scheme presented below:

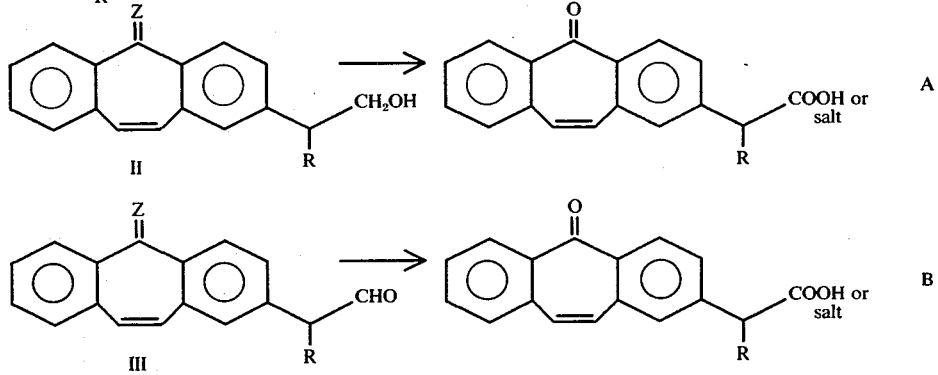

wherein R is as above and Z is oxo or a conventional ketal-protecting group.

In reaction scheme A is depicted the oxidation of a 5-oxo- or ketal-protected oxo-alcohol to the keto acid or salt of formula I. In reaction scheme B is depicted the oxidation of a 5-oxo- or ketal protected oxo-aldehyde to the keto acid or salt of formula I.

As oxidizing agents which are suitable for effecting the oxidation of an alcohol or aldehyde to an acid there may be mentioned the chromic (VI) oxidizing agents such as chromic acid, chromic oxide and alkali metal chromates and dichromates; alkali metal permanganates; nickel peroxide; and the like. Oxidizing agents specific for oxidizing aldehydes to acids are silver oxide, and the like. For effecting an oxidization of a ketal-protected starting material of formula II or III to a free keto acid of formula I it is necessary to utilize an oxidizing agent under acidic conditions. Particularly preferable oxidizing agents for effecting this conversion are chromic acid containing reagents such as, for example, aqueous chromic acid, chromic acid-sulfuric acid, chromic acid-acetic acid, and Jones reagent (chromic acid-acetone). Jones reagent is particularly preferred for effecting all of the above-mentioned oxidations.

For the conversion of an alcohol of formula II to the acid or salt of formula I, two equivalents of oxidizing agent are needed, whereas the oxidation of an aldehyde of formula III to the acid or salt of formula I requires only 1 equivalent of oxidizing agent.

The oxidation reaction may be carried out in an aqueous solvent, or in an inert organic solvent, or in a mixture of the above. Many solvent systems, neutral, acidic and basic, both homogeneous and 2-phase, for the use of chromic (VI) reagents are known in the art, such as acetic acid, water, acetone, pyridine, dichloromethane, dimethylformamide, and mixtures thereof. Details of the use of various chromic (VI) reagents for oxidation may be found, in summary form, in Fieser, "Reagents for Organic Synthesis", Vol. 1, John Wiley & Sons, Inc., (1967), pp. 142–147.

As mentioned above, the use of Jones reagent as an oxidant is preferred for the present process. For this oxidation, the reagent, normally an 8N solution of chromic acid and sulfuric acid in water, is titrated into a solution of the starting compound to be oxidized in acetone, at a temperature between about 0° and about 25° C. Completion of oxidation is normally noted by the change in color of the reaction mixture from orange-red to green.

After completion of the oxidation the desired acid may be obtained by conventional procedures such as extraction and crystallization.

Oxidation carried out under basic conditions results, initially, in the formation of a salt of the acid of formula I. The salt may be isolated by, e.g., evaporation of the solvent and crystallization or, more conveniently, it is converted to the free acid by acidification of the reaction mixture, and the free acid is isolated by conventional methods such as extraction and crystallization.

The starting materials for reaction schemes A and B, above, may be prepared as follows:

An ester of o-toluic acid may be brominated to afford the corresponding benzyl bromide which may then be converted to the triphenylphosphonium bromide. This may then be condensed, in a Wittig reaction, with the appropriate metasubstituted (methyl, ethyl or n-propyl) benzaldehyde to afford a 3'-alkylstilbene-2-carboxylic acid, after hydrolysis of the ester function. This may then be hydrogenated and the product cyclized with, for example, polyphosphoric acid, to afford a 2-alkyl-10,11-dihydro-5H-dibenzo[a,d]cyclohepten-5-one. This compound may be converted to the 10,11-dehydro compound by bromination with, for example, N-bromosuccinimide, followed by dehydrobromination with, for example, diazabicyclononene in dimethylformamide. The benzylic position of the alkyl group may be brominated with, for example, N-bromosuccinimide, in carbon tetrachloride. The bromo compound may then be converted to the corresponding triphenylphosphonium salt by reaction with triphenylphosphine. The triphenylphosphonium salt may then be converted to the corresponding 2-vinyl, 2-(2-propenyl) or 2-(2-butenyl) compound by a Wittig reaction with formaldehyde. The above mentioned olefin can then be converted to a 5-oxo alcohol of formula II by hydroboration with diborane in tetrahydrofuran followed by alkaline hydrogen peroxide oxidation. A 5-ketal protected oxo alcohol of formula II may be prepared by first ketalizing the keto olefin with, for example, phosphorus pentachloride, followed by ethylene glycol and triethylamine, and then hydroborating as above.

A 5-keto aldehyde of formula III may be prepared by, for example, oxidation of the corresponding keto alcohol of formula II with one equivalent of chromic oxide/pyridine (Collins oxidation). A 5-ketal protected oxo aldehyde of formula III may be prepared from the corresponding alcohol by, for example, oxidation with silver carbonate or celite.

The following examples illustrate preferred embodiments of the processes of the present invention. They should not be construed as limiting the scope or spirit of the invention in any manner. The yields of product obtained from the present process vary, depending upon the choice of starting material, reagents, reaction condition, and workup. Generally, however, the yields are in the range of from 20 to about 90 percent.

PREPARATION 1

A. 118 Gm. of methyl o-toluate and 140 gm. of N-bromosuccinimide are refluxed, using a heat lamp, in 1.3 l. of carbon tetrachloride for one hour. The solution is cooled and filtered and the solvent removed under vacuum. The residual liquid is dissolved in 500 ml. of acetonitrile and 250 gm. of triphenylphosphine is added. The mixture is warmed then cooled and the o-carbomethoxybenzyltriphenylphosphonium bromide is filtered off (yield 271 gm., 69%).

116.5 Gm. of 1,5-diazabicyclo[3.4.0]nonene-5 is added to 107.5 gm. of m-tolualdehyde and 400 gm. of o-carbomethoxybenzyltriphenylphosphonium bromide in 2000 ml. of acetonitrile. The mixture is refluxed briefly then cooled and the solvent removed under vacuum. The residue is dissolved in chloroform and washed with dilute hydrochloric acid, and the solution dried and evaporated. The product is refluxed for 11 hours in a solution of 111 gm. potassium hydroxide in 1,000 ml. of water and 150 ml. of methanol. The solution is cooled and extracted with chloroform. The aqueous solution is acidified with concentrated hydrochloric acid and extracted with chloroform. The extract is dried and evaporated to give 177.5 gm. (91%) of 3'-methylstilbene-2-carboxylic acid (ca. 60:40 cis:-trans). Use of m-ethylbenzaldehyde instead of m-tolualdehyde gives a similar yield of 3'-ethylstilbene-2-carboxylic acid.

B. A solution of 53.0 gm. of 3'-methylstilbene-2-carboxylic acid in 230 ml. dimethylformamide containing 2.0 gm. of 5% palladium on carbon is hydrogenated in a Parr shaker at 60 p.s.i. for 1½ hours. The solution is filtered and added to ether and water. The organic layer is washed with water, then dried and evaporated. The product is recrystallized from ether-hexane to give 48 gm., 90%, of 3-(o-carboxyphenethyl)toluene, m.p. 82°–84° C. Use of 3'-ethylenestilbene-2-carboxylic acid gives a similar yield of 3-(o-carboxyphenethyl)ethylbenzene.

C. 75 Gm. of 3-(o-carboxyphenethyl)toluene is dissolved in 400 ml. sulpholane and heated to 110°–120° C. 200 Ml. of polyphosphoric acid is added and the mixture is stirred at 100° C. for 90 minutes, and then poured onto ice and water. The mixture is extracted with hexane and the solution dried and evaporated to give 64 gm., 89%, of 2-methyl-10,11-dihydro-5H-dibenzo[a,d]cyclohepten-5-one as an oil. Use of 3-(o-carboxyphenethyl)ethylbenzene gives a similar yield of 2-ethyl-10,11-dihydro-5H-dibenzo[a,d]cyclohepten-5-one.

D. 60.5 Gm. of 2-methyl-10,11-dihydro-5H-dibenzo[a,d]cyclohepten-5-one is refluxed in 500 ml. of carbon tetrachloride with 58.2 gm. of N-bromosuccinimide for 8 hours. The solution is cooled and filtered and the solvent removed under vacuum. The residue is dissolved in 200 ml. of dimethylformamide and 44 gm. of 1,5-diazabicyclo[3.4.0]nonene-5 is added. The mixture is heated to 80° C. for 20 minutes, then cooled and added to water. The solution is extracted with ether and the extract washed, dried and evaporated. The residue is recrystallized from acetone/hexane to afford 39.7 gm., 69% of 2-methyl-5H-dibenzo[a,d]cyclohepten-5-one, m.p. 78°–80° C. Use of 2-ethyl-10,11-dihydro-5H-dibenzo [a,d]cyclohepten-5-one gives a similar yield of 2-ethyl-5H-dibenzo[a,d]cyclohepten-5-one, m.p. 62°–64° C.

E. 39.7 Gm. of 2-methyl-5H-dibenzo[a,d]cyclohepten-5-one is refluxed in 1200 ml. of carbon tetrachloride with 35.2 gm. of N-bromosuccinimide for 14 hours, irradiating with a 100 watt incandescent lamp. The solution is cooled, filtered and evaporated. The residue is recrystallized from methylene chloride/hexane to afford 27.3 gm., 51%, of 2-bromomethyl-5H-dibenzo[a,d]cyclohepten-5-one, m.p. 128°–132° C. Use of 2-ethyl-5H-dibenzo[a,d]cyclohepten-5-one gives 80% of 2-(α-bromoethyl)-5H-dibenzo[a,d]cyclohepten-5-one, m.p. 93°–95° C.

PREPARATION 2

3.0 G. of 2-(α-bromoethyl)5H-dibenzo[a,d]cyclohepten-5-one and 2.7 g. of triphenylphosphine are refluxed for 2 hours in 60 ml. of acetonitrile. The solution is cooled and diluted with 180 ml. of ether. The product is filtered off and dried to give 4.0 g., 77%, of 1-(5H-dibenzo[a,d]cyclohepten-5-on-2-yl)ethyltriphenylphosphonium bromide, m.p. 245°–255° C.

Use of 2-bromomethyl-5H-dibenzo[a,d]cyclohepten-5-one gives a similar yield of 5H-dibenzo[a,d]cyclohepten-5-on-2-yl-methyltriphenylphosphonium bromide.

PREPARATION 3

3.35 Gm. of 1-(5H-dibenzo[a,d]cyclohepten-5-on-2-yl)ethyltriphenylphosphonium bromide is suspended in 60 ml. of acetonitrile and 2.0 ml. of 1,5-diazabicyclo[3.4.0]nonene-5 is added. Formaldehyde vapor, entrained in nitrogen, is then passed in until the red color is discharged. The mixture is added to water and extracted with ether. The extract is washed, dried and evaporated to give 1.39 gm., 94%, of 2-(2-propenyl)5H-dibenzo[a,d]cyclohepten-5-one, m.p. 72°–75° C.

Use of 5H-dibenzo[a,d]cyclohepten-5-on-2-yl-methyl triphenylphosphonium bromide gives a similar yield of 2-vinyl-5H-dibenzo[a,d]cyclohepten-5-one.

PREPARATION 4

0.5 Gm. of phosphorus pentachloride is added to a solution of 0.5 gm. of 2-(2-propenyl)5H-dibenzo[a,d]cyclohepten-5-one in 20 ml. of benzene, and the mixture is stirred for one hour, and then added to a mixture of 1.0 ml. of ethylene glycol, 1.0 ml. of triethylamine and 20 ml. of acetonitrile. After 2 hours the mixture is washed with water, dried and evaporated to give a nearly quantitative yield of 5,5-ethylenedioxy-2-(2-propenyl)5H-dibenzo[a,d] cycloheptene.

Use of 2-vinyl-5H-dibenzo[a,d]cyclohepten-5-one gives a similar yield of 5,5-ethylenedioxy-2-vinyl-5H-dibenzo[a,d]cycloheptene.

PREPARATION 5

1.67 Ml. of 1.0 molar borane in tetrahydrofuran is added to an ice-cooled solution of 1.23 gm. of 2-(2-propenyl) 5H-dibenzo[a,d]cyclohepten-5-one in 10 ml. of tetrahydrofuran. The mixture is stirred for 2 hours and then 5 ml. of 3.0 molar aqueous sodium hydroxide and 1.5 ml. of 30% hydrogen peroxide are added. The reaction is left for one hour and then water and ether are added. The ethereal layer is washed, dried and evaporated. The product is chromatographed on 50 gm. silica gel, eluting with 1:1 ether/hexane, so as to obtain a 50% yield of 2-(5H-dibenzo[a,d]cyclohepten-5-on-2-yl)propan-1-ol, m.p. (hexane) 63°–66° C.

Use of 2-vinyl-5H-dibenzo[a,d]cyclohepten-5-one gives a similar yield of 2-(5H-dibenzo[a,d]cyclohepten-5-on-2-yl)ethanol, m.p. (hexane) 73°–75° C.

Use of 5,5-ethylenedioxy-2-(2-propenyl)5H-dibenzo[a,d] cycloheptene gives a similar yield of 2-(5,5-ethylenedioxy(5H-dibenzo[a,d]cyclohepten-2-yl)propan-1-ol.

Use of 5,5-ethylenedioxy-2-vinyl-5H-dibenzo[a,d]cycloheptene gives a similar yield of 5,5-ethylenedioxy-5H-dibenzo[a,d]cyclopenten-2-yl)ethanol.

PREPARATION 6

0.2 Gm. of chromium trioxide is added to a mixture of 12 ml. of methylene chloride and 1.2 ml. of pyridine at 0° C. A solution of 0.065 gm. of 2-(5H-dibenzo[a,d]cyclohepten-5-on-2-yl)propan-1-ol in 1 ml. of methylene chloride is added. After 45 minutes the solution is filtered through silica gel and evaporated to dryness. The residue is dissolved in 3 ml. of methanol containing 150 mg. of 1,2-dianilinoethane. After 3 hours the methanol is decanted from the deposited solid which is then shaken with ether and dilute hydrochloric acid. The ethereal layer is separated, washed, dried and evaporated to afford 0.022 gm., 31%, of 2-(5H-dibenzo[a,d]cyclohepten-5-on-2-yl)propionaldehyde.

Use of 2-(5H-dibenzo[a,d]cyclohepten-5-on-2-yl)ethanol gives a similar yield of 2-(5H-dibenzo[a,d]cyclohepten-5-on-2-yl)acetaldehyde.

PREPARATION 7

0.5 Gm. of 2-(5,5-ethylenedioxy-5H-dibenzo[a,d]cyclohepten-2-yl)propan-1-ol in 50 ml. of benzene, is refluxed for 6 hours with 4.0 gm. of silver carbonate on celite, prepared as described in Compt. Rendus. (1968) C, 267, 900a. The mixture is cooled and filtered and the solution evaporated to afford a 70% yield of 2-(5,5-ethylenedioxy-5H-dibenzo-[a,d]cyclohepten-2-yl)propionaldehyde.

Use of 2-(5,5-ethylenedioxy-5H-dibenzo[a,d]cyclohepten-2-yl)ethanol gives a similar yield of 2-(5,5-ethylenedioxy-5H-dibenzo[a,d]cyclohepten-2-yl)acetaldehyde.

EXAMPLE 1

0.1 Gm. of 2-(5H-dibenzo[a,d]cyclohepten-5-on-2-yl)propan-1-ol is dissolved in 5 ml. of acetone and the solution cooled to 0° C. under nitrogen. 0.189 ml. of 8N Jones reagent is added and the mixture is stirred for 2 hours. Water and ethyl acetate are added and the organic layer is washed with water then extracted with aqueous sodium carbonate. The extract is acidified with dilute hydrochloric acid and extracted with ethyl acetate; the organic layer is dried and evaporated to give 0.04 gm., 39%, of 2-(5H-dibenzo[a,d]cyclohepten-5-on-2-yl)propionic acid, m.p. (chloroformhexane) 138°–139° C.; m.p. (acetone-hexane) 113°–115° C.

Use of 2-(5H-dibenzo[a,d]cyclohepten-5-on-2-yl)ethanol gives a similar yield of 2-(5H-dibenzo[a,d]cyclohepten-5-on-2-yl)acetic acid, m.p. (acetone-hexane) 148°–149.5° C.

EXAMPLE 2

Using the conditions described in Example 1, 2-(5,5-ethylenedioxy-5H-dibenzo[a,d]cyclohepten-2-yl)propan-1-ol is converted, in similar yield, to 2-(5H-dibenzo[a,d]cyclohepten-5-on-2-yl)propionic acid and 2-(5,5-ethylenedioxy-5H-dibenzo[a,d]cyclohepten-2-yl)ethanol is converted in similar yield to 2-(5H-dibenzo[a,d]cyclohepten-5-on-2-yl)acetic acid.

EXAMPLE 3

0.4 Gm. of 2-(5H-dibenzo[a,d]cyclohepten-5-on-2-yl)-propionaldehyde is dissolved in 15 ml. of acetone and the solution is cooled to 0° C. under nitrogen. 0.4 ml. of 8N Jones reagent is added and the mixture is stirred for 2 hours, then diluted with water and extracted with ethyl acetate. The extract is washed with water then extracted with aqueous sodium carbonate. The aqueous solution is acidified with dilute hydrochloric acid and extracted with ethyl acetate. The ethyl acetate solution is dried and evaporated to yield 40% of 2-(5H-dibenzo[a,d]cyclohepten-5-on-2-yl)propionic acid, m.p. (chloroform-hexane) 138°–139° C.; m.p. (acetonehexane) 113°–115° C.

Use of 2-(5H-dibenzo[a,d]cyclohepten-5-on-2-yl)acetaldehyde gives a similar yield of 2-(5H-dibenzo[a,d]cyclohepten-5-on-2-yl)acetic acid, m.p. (acetone-hexane) 148°–149.5° C.

EXAMPLE 4

Using the conditions described in Example 3, 2-(5,5-ethylenedioxy-5H-dibenzo[a,d]cyclohepten-2-yl)propionaldehyde gives a similar yield of 2-(5H-dibenzo[a,d]cyclohepten-5-on-2-yl)propionic acid, and 2-(5,5-ethylenedioxy-5H-dibenzo[a,d]cyclohepten-2-yl)acetaldehyde gives a similar yield of 2-(5H-dibenzo[a,d]cyclohepten-5-on-2-yl)acetic acid.

What is claimed is:

1. A compound represented by the formula

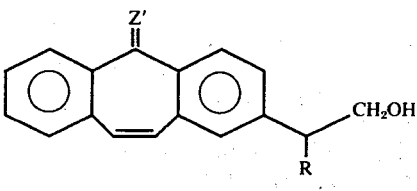

wherein R is hydrogen, methyl or ethyl and Z' is a conventional ketal protecting group selected from the group consisting of ethylene, 1,3-propylene, 2,2-dimethyl-1,3-propylene and 2,3-butylene.

2. The compound of claim 1 which is 2-(5,5-ethylenedioxy-5H-dibenzo[a,d]cyclohepten-2yl)-1-propanol.

3. A compound represented by the formula

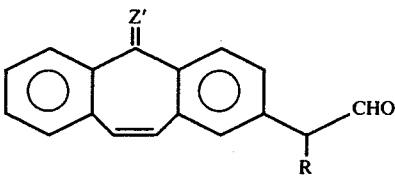

wherein R is hydrogen, methyl or ethyl and Z' is a conventional ketal protecting group selected from the group consisting of ethylene, 1,3-propylene, 2,2-dimethyl-1,3-propylene and 2,3-butylene.

4. The compound of claim 3 which is 2-(5,5-ethylenedioxy-5H-dibenzo[a,d]cyclohepten-2-yl)propionaldehyde.

* * * * *